United States Patent [19]

Cotteret et al.

[11] Patent Number: 4,929,439

[45] Date of Patent: May 29, 1990

[54] COSMETIC SCREENING COMPOSITION IN THE FORM OF AN OIL-IN-WATER EMULSION COMPRISING A UV-A SCREENING COMPOUND AND A UV-B SCREENING COMPOUND AND ITS USE FOR THE PROTECTION OF THE SKIN AGAINST ULTRA-VIOLET RADIATION

[75] Inventors: Jean Cotteret, Verneuil-sur-Seine; Jean F. Grollier, Paris, both of France

[73] Assignee: L'Oreal, Paris, France

[21] Appl. No.: 152,346

[22] Filed: Feb. 4, 1988

[30] Foreign Application Priority Data

Feb. 6, 1987 [LU] Luxembourg .......................... 86762

[51] Int. Cl.$^5$ .......................... A61K 7/40; A61K 7/42; A61K 7/44

[52] U.S. Cl. ........................................ 424/59; 424/60; 514/938; 514/939; 514/941; 514/942; 514/943

[58] Field of Search ...................... 424/59, 60; 514/938, 514/972

[56] References Cited

U.S. PATENT DOCUMENTS

| | | | |
|---|---|---|---|
| 3,479,428 | 11/1969 | Bryce et al. .......................... | 514/972 |
| 3,696,193 | 10/1972 | Guglielmetti et al. ................ | 424/59 |
| 3,781,417 | 12/1973 | Welters et al. ....................... | 514/972 |
| 3,816,611 | 6/1974 | Eberhardt et al. ................... | 514/972 |
| 4,254,104 | 3/1981 | Suzuki ................................. | 514/938 |
| 4,686,099 | 8/1987 | Palinezar ............................. | 424/59 |
| 4,731,200 | 3/1988 | Lang et al. .......................... | 424/59 |

FOREIGN PATENT DOCUMENTS

| | | | |
|---|---|---|---|
| 0085334 | 8/1983 | European Pat. Off. ............ | 514/938 |
| 2121801 | 1/1984 | United Kingdom ................. | 424/59 |
| 2123418 | 2/1984 | United Kingdom ................. | 424/59 |
| 2133985 | 8/1984 | United Kingdom ................. | 424/59 |
| 2170105 | 7/1986 | United Kingdom ................. | 424/59 |

*Primary Examiner*—Dale R. Ore
*Attorney, Agent, or Firm*—Fleit, Jacobson, Cohn, Price, Holman & Stern

[57] ABSTRACT

Cosmetic screening composition in the form of an oil-in-water emulsion comprising a UV-A screening compound and a UV-B screening compound and its use for the protection of the skin against ultraviolet radiation.

The invention relates to a cosmetic composition in the form of an oil-in-water emulsion which screens out UV rays of wavelengths of between 280 and 400 nm, which comprises partially or completely neutralized benzene-[1,4-bis(3-methylidenecamphomethylsulphonic acid)], in combination with N-(2-ethylhexyl)-4-(3-methylidenecamphor)benzenesulphonamide.

The sun protection composition of this kind possesses a high index of protection, enabling it to be used on skins that are very sensitive or continually exposed to solar radiation.

12 Claims, No Drawings

COSMETIC SCREENING COMPOSITION IN THE FORM OF AN OIL-IN-WATER EMULSION COMPRISING A UV-A SCREENING COMPOUND AND A UV-B SCREENING COMPOUND AND ITS USE FOR THE PROTECTION OF THE SKIN AGAINST ULTRA-VIOLET RADIATION

The present invention relates to a cosmetic composition which screens out ultraviolet radiation, in the form of an oil-in-water emulsion comprising a water-soluble UV-A screening agent in combination with an oil-soluble UV-B screening agent which are selected so as to increase the index of protection of the screening composition, as well as to the use of the said compsoition for protecting the human epidermis against ultraviolet radiation.

It is known that light radiation of wavelengths between 280 and 400 nm permit tanning of the human epidermis, and rays of wavelengths between 280 and 320 nm, known by the designation UV-B, also cause erythema and cutaneous burns which may jeopardize the development of the tan.

However, while the UV-B rays of wavelengths between 280 and 320 nm play a preponderant part in the production of solar erythema, and must be screened out, it remains nonetheless true that the UV-A rays of wavelengths between 320 and 400 nm, causing tanning of the skin, are also capable of producing adverse effects on the latter, especially in the case of sensitive skin or skin that is continually exposed to solar radiation. UV-A rays cause, in particular, a loss in elasticity of the skin and the appearance of wrinkles leading to premature ageing. They promote triggering of the erythematous reaction or enhance this reaction in some subjects, and can even be the source of phototoxic or photoallergic reactions. It may hence be advantageous to screen out all radiation of wavelengths between 280 and 400 nm.

Thus, the use has already been proposed of active compounds which strongly absorb UV rays over a wide band, including, more especially, benzene[bis-(methylidenecamphor)] derivatives sulphonated on the methyl radical at the 10-position of the camphor, such as those described in the Applicant's French Patent No. 2,528,420. These screening agents strongly absorb UV rays of wavelengths between 280 and 400 nm, with absorption maxima of between 320 and 400 nm for the compounds having methylidene camphor radicals present in the paraposition with respect to the benzene ring, and in particular in the region of 345 nm.

The efficacy of the cosmetic compositions containing these broad-spectrum UV screening agents, expressed in the sun protection factor appropriately referred to as the "index of protection or IP", is good, but still proves to be insufficient for skins that are very sensitive or continually exposed to solar radiation.

The index of protection or IP may be expressed as the ratio of the irradiation time required for reaching the erythemogenic threshold with the UV screening agent to the irradiation time required for reaching the erythemogenic threshold without the UV screening agent.

Sulphonamides derived from 3-benzylidenecamphor have also been proposed, such as those described in the Applicant's French Patent No. 2,529,887, and more especially N-(2-ethylhexyl)-4-(3-methylidenecamphor)-benzenesulphonamide. These screening agents strongly absorb UV rays of wavelengths between 280 and 380 nm, with absorption maxima most frequently of between 280 to 320 nm, N-(2-ethylhexyl)-4-(3-methylidenecamphor)-benzenesulphonamide having an absorption maximum at 294 nm.

However, the index of protection of cosmetic compositions containing the latter screening agent is, in this instance also, insufficient in the case of extremely sensitive skins.

Moreover, at the industrial level, it is naturally advantageous to have the possibility of using UV screening agents which, at low concentrations, enable sun protection compositions to be obtained having a high index of protection.

The applicant has just discovered that, by combining in an oil-and-water emulsion, the benzene[bis(methylidenecamphor)] derivative sulphonated on the methyl radical in the 10- position of the camphor consisting of benzene-[1,4-bis-(3-methylidenecamphomethylsulphonic acid)], which is a UV-A screening agent having an absorption maximum of 342 nm, with a sulphonamide derived from 3-benzylidenecamphor consisting of N-(2-ethylhexyl)-4-(3-methylidenecamphor)-benzenesulphonamide, which is a UV-B screening agent having an absorption maximum at 294 nm, there was obtained, surprisingly, for an oil-in-water emulsion containing a given concentration of the above-mentioned two screening agen in combination, an index of protection higher than the indices of protection of oil-in-water emulsions containing either of these two screening agents at the same concentration and in the same vehicle.

The subject of the present invention is hence a cosmetic composition which screens out ultraviolet radiation of wavelengths of between 280 and 400 nm containing, in an oil-in-water emulsion, partially or completely neutralized benzene-[1,4-bis(3-methylidenecamphomethyl sulphonic acid)] in combination with N-(2-ethylhexyl)-4-(3-methylidenecamphor)benzenesulphonamide.

The subject of the present invention is also a process for protecting the human epidermis against ultraviolet radiation of wavelengths between 280 and 400 nm, consisting in applying on the skin an effective amount of the abovementioned screening composition in the form of an oil-in-water emulsion comprising partially or completely neutralized benzene-[1,4-bis(3-methylidenecamphomethylsulphonic acid)] in combination with N-(2-ethylhexyl)-4-(3-methylidenecamphor) benzenesulphonamide.

To neutralize the benzene-[1,4-bis(3-methylidenecamphomethylsulphonic aicd)], it is possible to use alkali metal hydroxides and more especially those of sodium or potassium, ammonia solution and alkanolamines, triethanolamine being preferred.

The cosmetic screening compositions according to the invention possess, in addition, the advantage of being heat-stable and photochemically stable, of not being toxic and of being completely harmless with respect to the skin.

The oil-in-water sun protection emulsions according to the invention contain partially or completely neutralized benzene-[1,4-bis(3-methylidene-camphomethylsulphonic acid)], which is a water-soluble compound, in the aqueous phase. It is used in production, calculated in terms of the acid, of between 0.1 and 10% by weight, and preferably between 0.5 and 7.5% by weight, and more especially between 2 and 5%, based on the total weight of the composition.

The oil-in-water sun protection emulsions according to the invention contain N-(2-ethylhexyl)-4-(3-methylidenecamphor)benzenesulphonamide, which is a fatsoluble compound, in the oil phase, in proportions of between 0.5 and 10% by weight and preferably between 1 and 10% by weight, and more especially between 2 and 5% by weight, based on the total weight of the composition.

The pH of these emulsions is between 4 and 9, and preferably between 5.5 and 8. It may be adjusted by means of a customary alkalinizing or acidifying agent.

The fatty phase of the oil-in-water emulsions according to the invention represents approximately 15 to 60% of the total weight of the emulsion and consists of fats such as:

mineral oils such as liquid paraffin,
modified or unmodified vegetable or animal oils such as sweet-almond oil, avocado oil, oil of calophyllum, castor oil, olive oil, lanolin and its derivatives, perhydrosqualene, groundnut oil, wheatgerm oil, linseed oil, jojoba oil, apricot-kernal oil, walnut oil, palm oil, pistachio oil, sesame oil, rapeseed oil, cade oil, corn oil, peach-kernel oil, poppy-seed oil, pine-tar oil, soybean oil, safflower oil, coconut oil, hazelnut oil, grape pip oil, or alternatively sunflower oil:

saturated or unsaturated fatty acid esters or synthetic oils such as ethyl or isopropyl palmitate, alkylmyristates such as isopropyl, butyl and cetyl myristates, hexyl stearate, triglycerides of $C_8$–$C_{18}$ fatty acids, cetyl ricinoleate, stearyl octanoate (Purcellin oil), cetyl/stearyl 2-ethylhexanoate, esters of fatty acids and glycerol and hydrogenated polyisobutane.

The oil phase of the emulsions according to the invention can also contain certain waxes, and in particular carnauba wax, beeswax, ozokerite, candelilla wax and microcrystalline waxes, or silicone oils, for example dimethylpolysiloxane, or alternatively $C_{12}$–$C_{18}$ fatty alcohols and fatty acids.

The aqueous phase of the oil-in-water emulsion according to the invention represents approximately 40 to 85% of the total weight of the emulsion.

The aqueous phase of the water-in-oil emulsions according to the invention can also contain lower monohydric alcohols or polyhydric alcohols containing 1 to 6 carbon atoms. The monohydric or polyhydric alcohols that are especially preferred are ethanol, isopropanol, propylene glycol and glycerin.

The emulsifiers are present either in the fatty phase or in the aqueous phase, or in both phases at once when a mixture is used.

The proportion of emulsifiers is generally between 1 and 15% based on the total weight of the emulsion.

These emulsifiers are chosen from:
polyoxyethylenated ($C_8$–$C_{12}$ alkyl)phenols containing 9 to 15 mols of ethylene oxide;
polyoxyethylenated $C_{12}$–$C_{18}$ fatty alcohols containing at least 4 and preferably 4 to 35 ethoxy units;
polyglycerolated $C_{10}$–$C_{18}$ fatty alcohols containing 4 to 10 glycerol units;
polyethoxylated and polyglycerolated $C_{12}$–$C_{18}$ fatty acid esters;
polyoxyethylenated $C_{12}$–$C_{18}$ fatty acid esters of sorbitan containing 10 to 20 moles of ethylene oxide;
propylene oxide/ethylene oxide copolymers;
soybean or egg-yolk lecithin;
$C_{12}$–$C_{18}$ fatty acid esters of polyethylene glycol containing at least two ethoxy units and preferably 4 to 20 ethoxy units;
polyoxyethylenated castor oil containing 10 to 60 mols of ethylene oxide;
sucroglycerides;
soaps;
phosphoric esters of fatty alcohols;
sulphates of fatty alcohols, optionally oxyethylenated;
polyoxyethylenated lanolin alcohols containing at least 4 ethoxy units.

The oil-in-water emulsions according to the invention can also contain thickeners, emollients, humectants, surfactanats, preservatives, anti-foaming agents, perfurmes, colourings of pigments whose function is to colour the composition itself or the skin, or any other ingredient customarily used in cosmetics.

These oil-in-water emulsions can be presented in different forms, such as a milk or a cream, and can be packaged as an aerosol.

These emulsions can also contain, in addition to the combination of the two screening agents according to the invention, other well-known water-soluble or oil-soluble UV screening agents such as, by way of example, coffee oil, salicylic acid derivatives, cinnamic acid derivatives, esters and derivatives of p-aminobenzoic acid, anthranilates, benzophenone derivatives, camphor derivatives such as p-methylbenzylamine camphor, dibenzoylmethane derivatives, benzotriazole derivatives, benzoxazole derivatives and benzimidazole derivatives.

The invention will be more readily understood by means of the non-limiting examples which follow.

EXAMPLE 1

The following sun protection composition is prepared:

| A - Fatty phase | |
|---|---|
| Lanolin | 8.0 g |
| Triester of glycerine and $C_{10}$–$C_{18}$ fatty acid | 5.5 g |
| Ester of polyethoxylated oleic acid and glycerol sold by the Company GATTEFOSSE under the name "LABRAFIL M 1969 CS" | 3.0 g |
| Mixture of glyceryl stearate and polyethylene glycol 100 stearate | 5.0 g |
| Cetyl alcohol | 1.0 g |
| Stearic acid | 2.5 g |
| Triethanolamine | 0.2 g |
| Mixture of cetyl phosphate and cetyl diethanolamine phosphate sold under the name "AMPHISOL" by the company GIVAUDAN | 0.5 g |
| Mixture of cetyl/stearyl 2-ethylhexanoate and isopropyl myristate | 4.0 g |
| Sunflower oil | 4.0 g |
| N-(2-Ethylhexyl)-4-(3-methylidenecamphor) benzenesulphonamide | 2.5 g |
| Perfume, preservative qs | |
| | 36.2 g |
| B - Aqueous phase | |
| Benzene-[1,4-bis(3-methylidenecamphomethylsulphonic acid)] | 2.5 g |
| Triethanolamine | 1.7 g |
| Preservative qs | |
| Water | 59.6 g |

The emulsion is produced by adding the fatty phase A brought to about 80° C., to the aqueous phase B brought to the same temperature and with rapid agitation. An oil-in-water emulsion is obtained which takes the form of a cream.

EXAMPLE 2

The following sun protection composition is prepared:

| A - Fatty phase | |
| --- | --- |
| Non-self-emulsifying glycerol mono- and distearate | 2 g |
| Polydimethylsiloxane | 1.5 g |
| Cetyl alcohol | 1.5 g |
| Miglyol 812: triglycerides of $C_8$–$C_{12}$ fatty acids | 30 g |
| Cetyl/stearyl alcohol | 5.6 g |
| Cetyl/stearyl alcohol oxyethylenated with 33 mols of ethylene oxide | 1.4 g |
| N-(2-Ethylhexyl)-4-(3-methylidenecamphor)-benzenesulphonamide | 2.5 g |
| Perfume, preservative qs. | |
| | 44.5 g |
| B - Aqueous phase | |
| Benzene-[1,4-bis(3-methylidenecamphormethylsulphonic acid)] | 2.5 g |
| Triethanolamine | 1.7 g |
| Glycerine | 20 g |
| Preservative qs. | |
| Water | 31.30 g |

The emulsion is produced in the same manner as in Example 1. An oil-in-water emulsion is obtained which takes the form of a cream.

EXAMPLE 3

The following sun protection composition is prepared:

| A. Fatty phase | |
| --- | --- |
| Lanolin | 8.00 g |
| Triester of glycerin and $C_{10-18}$ fatty acid | 5.50 g |
| Ester of polyethoxylated oleic acid and glycerol sold by the company GATTEFOSSE under the name "LABRAFIL M 1969 CS" | 3.00 g |
| Mixture of glyceryl stearate and polyethylene glycol 100 stearate | 5.00 g |
| Cetyl alcohol | 1.00 g |
| Stearic acid | 2.50 g |
| Triethanolamine | 0.20 g |
| Mixture of cetyl phosphate and cetyl diethanolamine phosphate sold by the company GIVAUDAN under the name "AMPHISOL" | 0.50 g |
| Mixture of cetyl/stearyl 2-ethyl hexanoate and isopropyl myristate | 4.00 g |
| Sunflower oil | 4.00 g |
| N-(2-Ethylhexyl)-4-(3-methylidenecamphor) benzene sulphonamide | 1.20 g |
| Perfume, preservative qs. | |
| | 34.90 g |
| B. Aqueous Phase | |
| Benzene-[1,4-bis(3-methylidenecamphomethylsulphonic acid)] | 1.20 g |
| Triethanolamine | 0.72 g |
| Preservative qs. | |
| Water | 65.10 g |

The emulsion is produced by adding the fatty phase A, brought to about 80° C., to the aqueous phase B brought to the same temperature and with rapid agitation. An oil-in-water emulsion is obtained which takes the form of a cream.

We claim:

1. In a sunscreening cosmetic composition that screens out ultraviolet radiation wavelengths between 280 and 400 nm. and that is in the form of an oil-in-water emulsion which contains 0.5 to 10% by weight of N-(2-ethylhexyl)-4-(3-methylidenecamphor) benzene sulfonamide in the oil phase of said emulsion, wherein said oil phase consists essentially of fats selected from the group consisting of modified mineral oils, unmodified mineral oils, modified vegetable oils, unmodified vegetable oils, modified animal oils, and unmodified animal oils, and waxes, esters of saturated fatty acids, esters of unsaturated fatty acids, synthetic oils, and $C_{12}$–$C_{18}$ fatty alcohols and acids, wherein the improvement comprises adding 0.1 to 10% by weight of partially or fully neutralized benzene-[1,4-bis(3-methylidenecamphomethylsulphonic acid] to the aqueous phase of said emulsion, whereby the protection index of said sunscreening composition is increased.

2. Cosmetic screening composition according to claim 1, which comprises 2 to 5% by weight of benzene-[1,4-bis(3-methylidenecamphomethylsulphonic acid)] before partial or complete neutralization and 2 to 5% by weight of N-(2-ethylhexyl)-4-(3-methylidenecamphor)-benzenesulphonamide, based on the total weight of the emulsion.

3. Cosmetic screening composition according to claim 1, wherein the benzene-[1,4-bis(3-methylidenecamphomethylsulphonic acid)] is partially or completely neutralized with an alkali metal hydroxide, ammonia solution or an alkanolamine.

4. Cosmetic screening composition according to claim 1, which has a pH of between 4 and 9.

5. Cosmetic screening composition according to claim 1, wherein the fatty phase of the emulsion represents approximately 15 to 60% and the aqueous phase approximately 40 to 85% of the total weight of the emulsion.

6. Cosmetic screening composition according to claim 1 wherein the aqueous phase of the emulsion comprises, in addition to water, $C_1$ to $C_6$ lower monohydric or polyhydric alcohols.

7. Cosmetic screening composition according to claim 1, wherein the proportion of emulsifiers is between 1 and 15% of the total weight of the emulsion, these emulsifiers being dissolved in the fatty phase or in the aqueous phase or distributed in both phases.

8. Cosmetic screening composition according to claim 7, wherein the emulsifiers are selected from the group consisting of polyoxyethylenated ($C_8$–$C_{12}$ alkyl)-phenols containing 9 to 15 mols of ethylene oxide, polyoxyethylenated $C_{12}$–$C_{18}$ fatty alcohols containing at least 4 ethoxy units, polyglycerolated $C_{10}$–$C_{18}$ fatty alcohols containing 4 to 10 glycerol units, polyoxyethylenated and polyglycerolated $C_{12}$–$C_{18}$ fatty acid esters, polyoxyethylenated $C_{12}$–$C_{18}$ fatty acid esters of sorbitan containing 10 to 20 moles of ethylene oxide, propylene oxide/ethylene oxide copolymers, soybean lecithin, yolk lecithin, $C_{12}$–$C_{18}$ fatty acid esters of polyethylene glycol containing at least two ethoxy units, polyoxyethylenated castor oil containing 10 to 60 mols of ethylene oxide, soaps, phosphoric esters of fatty alcohols, sulphates of fatty alcohols, oxyethylenated, polyoxyethylenated lanolin alcohols containing at least 4 ethoxy units and sucroglycerides.

9. Cosmetic screening composition according to claim 1, which contains in addition, thickeners, emollients, humectants, surfactants, preservatives, anti-foaming agents, perfumes, colourings and pigments.

10. Cosmetic screening composition according to claim 1, which comprises, in addition, other water-soluble or oil-soluble IV screening agents selected from the group consisting of coffee oil, salicyclic acid derivatives, cinnamic acid derivatives, esters and derivatives of p-aminobenzoic acid, antrhanilates, benzophenone derivatives, camphor derivatives, dibenzoylmethane derivatives, benzotriazole derivatives, benzoxazole derivatives and benzimidazole derivatives.

11. Cosmetic screening composition according to claim 1, which is in the form of milk or cream.

12. A process for the protection of the human epidermis against ultraviolet radiation of wavelengths between 280 and 400 nm., comprising applying an effective amount of a sunscreening cosmetic composition to the skin, wherein said composition screens out ultraviolet radiation wavelengths between 280 and 400 nm. and is in the form of an oil-in-water emulsion comprising 0.5 to 10% by weight of N-(2-ethylhexyl)-4-(3-methylidenecamphor) benzene sulfonamide in the oil phase of said emulsion and 0.1 to 10% by weight of partially or fully neutralized benzene-[1,4-bis(3-methylidenecamphomethylsulphonic acid] in the aqueous phase of said emulsion, wherein said oil phase consists essentially of fats selected from the group consisting of modified mineral of, unmodified mineral oils, modified vegetable oils, unmodified vegetable oils, modified animal oils, unmodified animal oils, and waxes, esters of saturated fatty oils, esters of unsaturated fatty acides, synthetic oils, and $C_{12}$–$C_{18}$ fatty alochols and acids.

* * * * *